United States Patent [19]

Sunshine et al.

[11] Patent Number: 4,656,177

[45] Date of Patent: Apr. 7, 1987

[54] ANALGESIC AND ANTI-INFLAMMATORY COMPOSITIONS COMPRISING CAFFEINE AND METHODS OF USING SAME

[75] Inventors: Abraham Sunshine, New York; Eugene M. Laska, Larchmont; Carole E. Siegel, Mamaroneck, all of N.Y.

[73] Assignee: Analgesic Associates, Larchmont, N.Y.

[21] Appl. No.: 839,986

[22] Filed: Mar. 17, 1986

Related U.S. Application Data

[60] Division of Ser. No. 643,196, Aug. 22, 1984, Pat. No. 4,587,249, which is a division of Ser. No. 474,358, Mar. 11, 1983, Pat. No. 4,486,436, which is a continuation of Ser. No. 400,597, Jul. 22, 1982, abandoned.

[51] Int. Cl.$^4$ .................. A61U 31/40; A61U 31/52
[52] U.S. Cl. ........................ 514/264; 514/408; 514/420
[58] Field of Search .................. 514/420, 264, 408

[56] References Cited

U.S. PATENT DOCUMENTS

| | | | |
|---|---|---|---|
| 4,234,601 | 11/1980 | Gardocki | 514/567 |
| 4,237,140 | 12/1980 | Dudzinski | 514/567 |
| 4,322,427 | 3/1982 | Buyniski et al. | 514/567 |
| 4,379,789 | 4/1983 | Capetola et al. | 514/569 |
| 4,439,094 | 4/1969 | Emele | 514/263 |

OTHER PUBLICATIONS

Chemical Abstracts, vol. 96, No. 18, (May 3, 1982) No. 149162u, JP, A, 81154416.
Chemical Abstracts, vol. 72, No. 2, (Jan. 18, 1965) W. O. Evans, "The Potentiation of Opiate-Induced Analgesia by Stimulant Drugs, I. The Effect of Manoamine Oxidase Inhibitors and Caffeine".
Unlisted Drugs, vol. 32, No. 3, (Mar. 1980) p. 41j "Kofesil".
Unlisted Drugs, vol. 29, No. 6 (Jun. 1977) p. 91t "Nurodol".
Unlisted Drugs, vol. 24, No. 6, (Jun. 1972) p. 84p "Coffoselt".
Unlisted Drugs, vol. 29, No. 3, (Mar. 1976) p. 37e "Albaton".
Unlisted Drugs, vol. 16, No. 8, (Aug. 1964) p. 56L "Femadol Co.".
Unlisted Drugs, vol. 25, No. 7, (Jul. 1973) p. 110h "Ergoffen".
Dictionnaire Vidal, (1982), O.V.P. (Paris, FR) p. 716 "Lamaline au Paracetamol".
Rote Liste, (1961) Editio Cantor (Aulendorf/Wurtt., DE) p. 716 "Phenacodin".

*Primary Examiner*—Stanley J. Friedman
*Attorney, Agent, or Firm*—Burns, Doane, Swecker & Mathis

[57] ABSTRACT

Novel analgesic and anti-inflammatory compositions of matter for use in eliciting an analgesic or anit-inflammatory response, said compositions comprising caffeine together with a selected non-narcotic analgesic/non-steroidal anti-inflammatory drug or a selected narcotic analgesic, or both, are disclosed. When used in combination with the selected drugs, caffeine enhances the analgesic or anti-inflammatory response and also hastens its onset.

24 Claims, No Drawings

ANALGESIC AND ANTI-INFLAMMATORY COMPOSITIONS COMPRISING CAFFEINE AND METHODS OF USING SAME

CROSS-REFERENCE TO RELATED APPLICATIONS

This application is a division of Ser. No. 643,196, filed Aug. 22, 1984, now U.S. Pat. No. 4,587,249, which is a division of Ser. No. 474,358, filed Mar. 11, 1983, now U.S. Pat. No. 4,486,436, which is a continuation of Ser. No. 400,597, filed July 22, 1982, now abandoned.

The subject matter of this application is related to that of our patent applications entitled "IMPROVED ANALGESIC COMPOSITIONS COMPRISING PROPIRAM AND METHODS OF USING SAME" Ser. No. 488,815 filed 4-26-83, now U.S. Pat. No. 4,479,956 and IMPROVED ANALGESIC AND ANTI-INFLAMMATORY COMPOSITIONS COMPRISING IBUPROFEN AND METHODS OF USING SAME" Ser. No. 400,645, filed 7-22-82 now U.S. Pat. No. 4,420,483, both incorporated by reference herein and relied upon.

FIELD OF THE INVENTION

The present invention relates to novel pharmaceutical compositions of matter comprising caffeine and one or more analgesic agents, or caffeine and an anti-inflammatory agent, and to methods of using said compositions to hasten the onset of an analgesic or anti-inflammatory response and to enhance an analgesic or anti-inflammatory response.

BACKGROUND ART

Non-narcotic analgesics, most of which are also known as non-steroidal anti-inflammatory drugs (NSAID), are widely administered orally in the treatment of mild to severe pain. Within this class, the compounds vary widely in their chemical structure and in their biological profiles as analgesics, anti-inflammatory agents and antipyretic agents. Aspirin, acetaminophen and phenacetin have long been among the most commonly used members of this group; more recently, however, a large number of alternative non-narcotic agents offering a variety of advantages over the earlier drugs have been developed. Tolerance or addiction to these drugs is not generally a problem with their continuous use in the treatment of pain or in the treatment of acute or chronic inflammatory states (notably, rheumatoid arthritis and osteoarthritis); nevertheless, these drugs generally have a higher potential for adverse side-effects at the upper limits of their effective dose ranges. Moreover, above each drugs's upper limit or ceiling, administration of additional drug does not usually increase the analgesic or anti-inflammatory effect. Among the newer compounds in the non-narcotic analgesic/nonsteroidal anti-inflammatory group are compounds such as diflunisal (Dolobid ®), zomepirac sodium (Zomax ®), ibuprofen (Motrin ®), naproxen (Naprosyn ®), fenoprofen (Nalfon ®), piroxicam (Feldene ®), flurbiprofen, mefenamic acid (Ponstel ®) and sulindac. See also *Physician's Desk Reference*, 35th edition, 1981, and *The Merck Index*, ninth edition, Merck & Co., Rahway, N.J. (1976), for information on specific nonsteroidal anti-inflammatory agents. Also see, generally, Wiseman, "Pharmacological Studies with a New Class of Nonsteroidal Anti-Inflammatory Agents—The Oxicams—With Special Reference to Piroxicam (Feldene ®), *The American Journal of Medicine*, Feb. 16, 1982: 2–8; Foley et al, *The Management of Cancer Pain, Volume II—The Rational Use of Analgesics in the Management of Cancer Pain*, Hoffman-LaRoche Inc., 1981; and *Cutting's Handbook of Pharmacology*, sixth edition, ed. T. Z. Czáky, M.D., Appleton-Century-Crofts, New York, 1079, Chapter 49: 538–550.

Narcotic analgesics are often used when pain control with non-narcotic analgesics is ineffective. While the drugs in this group vary considerably in their chemical structures and pharmacological properties, almost all suffer the disadvantages of tolerance and possible addiction with continued usage. Within the narcotic analgesic group, the drugs can be classified as narcotic agonists or narcotic antagonists. Narcotic agonists include the morphine group, the meperidine group and the methadone group. While some narcotic antagonists are pure antagonists (which are not analgesics), other narcotic antagonists are agonist-antagonists (i.e. antagonists with analgesic properties); the agonist-antagonists are generally categorized as morphine-like or nalorphine-like). Many of the narcotic analgesics are not effective orally, but are rather used parenterally. The orally active narcotic analgesics include such compounds as codeine, oxycodone, levorphanol (Levo-Dromoran ®), meperidine (Demerol ®), propoxyphene hydrochloride (Darvon ®), propoxyphene napsylate (Darvon-N ®), methadone, propiram, buprenorphine, pentazocine (Talwin ®), nalbuphine (Nubain ®) and butorphanol (Stadol ®). For more specific information on these compounds, see *Physicians' Desk Reference*, 35th edition, 1981, and *The Merck Index*, ninth edition, Merck & Co., Inc., Rahway, N.J (1976). Also see, generally, the Foley et al reference cited hereinabove and *Cutting's Handbook of Pharmacology*, sixth edition, ed. T. Z. Czáky, M.D., Appleton-Century-Crofts, New York, 1979, Chapter 50: 551–566.

Caffeine, or 3,7-dihydro-1,3,7-trimethyl-1H-purine-2,6-dione, has the structural formula

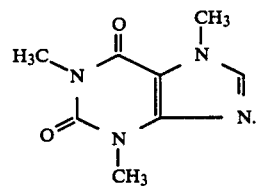

This substance has been used alone, intravenously, in the treatment of headaches and has also been used in combination with selected drugs. Compositions containing one or more of the analgesics aspirin, acetaminophen and phenacetin in combination with varying amounts of caffeine have been marketed in the past; in several cases, such non-narcotic analgesic/caffeine combination products have further included one of the narcotic analgesics codeine, propoxyphene or oxycodone. Examples of these combinations include the products known commercially as Excedrin ®, SK-65 ® Compound, Darvon ® Compound, Anacin ®, A.P.C., and A.P.C. with Codeine, Tabloid ® Brand. The non-steroidal analgesic components of these mixtures have the following structural formulas:

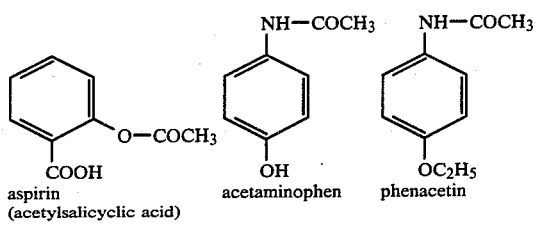

aspirin (acetylsalicyclic acid)  acetaminophen  phenacetin

The three narcotic analgesics which have occasionally been added to the aspirin/phenacetin/acetaminophen/caffeine combinations have the following structural formulas:

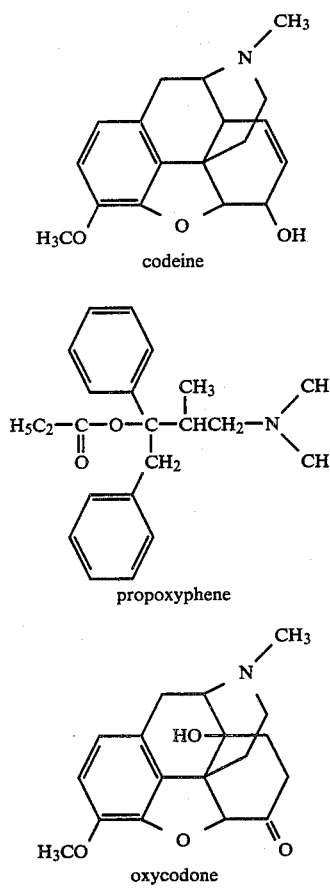

codeine propoxyphene oxycodone

As far as the present inventors know, however, the art has never suggested that caffeine be added to a narcotic analgesic to contribute to its analgesic effect.

Many workers have sought to demonstrate the efficacy of the aspirin/phenacetin/acetaminophen/caffeine combination products. An extensive review of the literature on caffeine and analgesics has been published ["Over-The-Counter Drugs: Establishment of a Monograph for OTC Internal Analgesic, Antipyretic and Antirheumatic Products," Federal Register, 1977, 42 (131): 35482-35485] and several relevant additional articles have appeared. Most animal studies on caffeine analgesia have been performed on the rat. Williams (Toxicology and Applied Pharmacology, 1959, 1: 447-453) utilized experimental pain and found that caffeine alone exerted analgesic effects on rats and when combined with aspirin; the effect appeared additive but not potentiating. Vinegar et al. (Proceedings of the Society for Experimental Biology and Medicine, 1976, 151: 556-560), ten years later, found that in the rat caffeine potentiates the acute anti-inflammatory and analgesic activity of aspirin. Siegers (Pharmacology, 1973, 10: 19-27) studied the effect of oral doses of caffeine (10, 50 and 100 mg/kg) given to rats together with acetaminophen and found that caffeine inhibited its absorption and lowered its serum concentration. He suggested that delayed stomach emptying as a result of the relaxing effect of caffeine on gastric smooth muscle was probably the cause of the diminished absorption of orally administered drugs in the presence of caffeine. Despite this finding, acetaminophen analgesia was not decreased by caffeine. In agreement with Williams and Vinegar and his associates, Siegers found that caffeine itself had analgesic activity. Only in the lowest dose of caffeine studied, a dose at which analgesia was not exhibited, was there a reduction in the acetaminophen induced analgesia. In a more recent paper, Seegers et al (Arch. Int. Pharmacodyn., 1981, 251: 237-254) demonstrated an anti-inflammatory, analgesic effect of caffeine in rats. He also found that the combination of caffeine, aspirin and acetaminophen as well as the combination of caffeine, aspirin and phenacetin at low doses produced anti-inflammatory, analgesic effects which are at least as great as would be expected on the basis of addition, while at high doses, the results suggested potentiation. Citing the work of Giertz and Jurna (Naturwissenschaften, 1957, 44: 445), and Fuchs and Giertz (Arzneimittelforsch, 1960, 10: 526-530), who observed that caffeine induced analgesia in assays in mice in which inflammation was not involved, Seegers asserted that, "it seems safe to assume that the analgesic activity of caffeine consists of at least two components, one independent of and another one dependent on its anti-inflammatory activity."

The earliest relevant study in humans was reported by Wallenstein (Proceedings of the aspirin symposium, held at the Royal College of Surgeons, London, 1975). Two tablets of a combination in which each tablet contained aspirin 210 mg, acetaminophen 150 mg and caffeine 30 mg, clearly and significantly produced more analgesia than the combination without caffeine. The one tablet dose of the combination had higher mean scores than either component alone, but was not superior to the combination without caffeine. Wallenstein speculated that, "dosage may be an important factor, and caffeine may simply be ineffective much below the 60 mg dose". Booy (Nederlands Tijdschrift Voor Tandheelkinde, 1972, 79: 69-75) studied pain relief on each of two days after tooth extraction. Patients who reported "great pain" on the first day obtained more pain relief from 1000 mg of acetaminophen plus 100 mg of caffeine than from 1000 mg of acetaminophen alone. On the second day this difference was not found, although on both days all treatments were superior to placebo. Lim et al (Clin. Pharmacol. Ther., 1967, 8: 521-542), reporting a study in which experimental pain was induced in the subjects by bradykinin, observed that the combination of aspirin 520 mg and acetaminophen 260 mg given orally could not be distinguished from placebo, whereas the same combination in lesser quantities, aspirin 325 mg and acetaminophen 162.5 mg plus caffeine 32.5 mg was significantly different from placebo at 15, 60, 75, 105, and 120 minutes after taking the drug. A double-blind, crossover study of 216 patients by Wojcicki et al [Archivum Immunologiae et Therapeae Experimentalis, 1977, 25(2): 175-179] compared the activity of 1000 mg of acetaminophen plus 100 mg of caffeine against the same quantity of acetaminophen alone. One group of patients in the trial were suffering severe and frequently occurring idiopathic headache and a second group had moderate post-operative orthopedic pain. The authors concluded that the relief of pain was far greater with the caffeine combination than with acetaminophen alone or with aspirin alone. Jain et al (*Clin. Pharmacol. Ther.*, 1978, 24: 69-75) first studied 70 postpartum patients with moderate to severe uterine cramp and/or episiotomy pain and then a second group of 70 patients limited to severe pain only. Comparing 800 mg aspirin plus 64 mg of caffeine to 650 mg aspirin alone, these authors concluded that in patients with severe episiotomy pain the combination is the more effective analgesic.

Caffeine use in the treatment of headache has a long history. The FDA Advisory Panel, in its review of caffeine [*Federal Register*, 1977, 42 (131): 35482-35485] argued that the known biochemical effect of caffeine on small blood vessels provides a plausible explanation for its effectiveness in treating headache associated with cerebral blood vessels. Recently Sechzer [*Curr. Therapy Research*, 1979, 26(4)] found that the intravenous administration of caffeine sodium benzoate rapidly provided relief in the majority of patients experiencing headache resulting from dural puncture or spinal anesthesia. The author, referring to the literature on the mechanism of action of caffeine on cerebral blood flow and on cerebral vascular tone, argues from the opposite perspective of the Panel that the analgesic relief obtained implies that an intracranial vascular component is the primary factor in such headaches.

Changes in mood and over-all sense of "well-being" after administration of caffeine have been widely reported in the literature. Beginning in the early part of this century, Hollingsworth (*Arch. Psychol.*, 1912, 22: 1) reported beneficial motor and mental effects from 65 to 130 mg of caffeine, and tremor, poor motor performance, and insomnia caused by 390 mg of caffeine. Many studies over the past 70 years have confirmed those findings. Review articles on the xanthines [Ritchie, J. M., "Central nervous system stimulants. 2. The xanthines," Goodman, L. S. & Gilman, A. (Eds.), *The pharmacological basis of therapeutics,* 4th Ed., New York: Macmillan Co., 1970; Stephenson, P. E., "Physiologic and psychotropic effects of caffeine on man," *J. Amer. Diet. Assoc.*, 1977, 71(3): 240-247] report that doses of 50 to 200 mg of caffeine result in increased alertness, decreased drowsiness, and lessened fatigue. Doses in the range of 200 to 500 mg may produce headaches, tremor, nervousness and irritability.

After extensively reviewing the relevant literature, the most significant contributions of which are summarized above, the FDA Advisory Panel in 1977 concluded that caffeine when used as an analgesic adjuvant was safe, but that there was insufficient data to demonstrate that caffeine contributes anything to the action of the analgesic [*Federal Register*, 1977, 42 (131): 35482-35485]. The Panel stated:

> Unfortunately, the information and data submitted, fail to demonstrate conclusively that caffeine in combination is effective as an analgesic, antipyretic and/or antirheumatic ingredient. The Panel finds there is little evidence to show that this ingredient even contributes to these pharmacological effects in the clinical situation.

This remains the official position on the question up to the present time. Consequently, many of the analgesic/caffeine combination products previously available are no longer on the market.

In addition to the few prior art instances of selected non-narcotic analgesic/caffeine combinations further containing a selected narcotic analgesic (which three-component combinations have already been discussed hereinabove), there also are examples in the art of two-component combinations of selected non-narcotic analgesics with selected narcotic analgesics. Known combinations of this type include Darvon ® with A.S.A. ® (propoxyphene hydrochloride and aspirin), Darvon-N ® with A.S.A. ® (propoxyphene napsylate and aspirin), aspirin with codeine, Talwin ® Compound (pentazocine hydrochloride, oxycodone and aspirin), Percodan ® (oxycodone hydrochloride, terephthalate and aspirin) and nalbuphine with acetaminophen, the last-mentioned combination being disclosed in U.S. Pat. No. 4,237,140. The general principle of use of a combination of drugs to produce additive analgesic effects is known to those skilled in the art; for example, Foley et al, *The Management of Cancer Pain, Volume II—The Rational Use of Analgesics in the Management of Cancer Pain,* Hoffman-LaRoche Inc., 1981, suggest such combination and specifically point out that 650 mg aspirin or acetaminophen regularly added to the standard narcotic dose will often enhance the analgesic effect without requiring higher doses of the narcotic. Such additive effects have been reported earlier by Houde et al, *Clin. Pharm. Ther.* 1(2): 163-174(1960) for intramuscularly administered morphine sulfate given with orally administered aspirin. As far as the present inventors know, however, the art does not suggest any two-component compositions of a narcotic analgesic and caffeine; it also does not suggest any improvements in the analgesic response to be derived from co-administering caffeine with any narcotic analgesic.

SUMMARY OF THE INVENTION

Surprisingly, the present inventors now find that selected non-narcotic analgesics/nonsteroidal anti-inflammatory drugs, which differ substantially in chemical structure from aspirin, phenacetin and acetaminophen, and which have significantly different biological profiles therefrom, can be advantageously formulated into novel pharmaceutical compositions together with caffeine and administered to mammals, especially humans, to not only elicit a more potent analgesic or anti-inflammatory response but also to evoke such response more rapidly than possible by administration of the analgesic or anti-inflammatory agent alone.

The present inventors also find, quite surprisingly, that orally effective narcotic analgesics (i.e. narcotic agonists and narcotic agonist-antagonists which are effective orally as analgesics) can likewise be advantageously formulated into novel pharmaceutical compositions together with caffeine and administered to mammals, especially humans, to not only elicit a more potent analgesic response but also to evoke such response more rapidly than possible by administration of the narcotic drug alone. The present inventors further find that orally effective narcotic analgesics can be advantageously combined with non-narcotic analgesics and caffeine to form novel pharmaceutical compositions which can be administered to mammals, especially humans, to elicit an improved analgesic response.

In one aspect, the present invention thus provides a novel pharmaceutical composition of matter for use in eliciting an analgesic or anti-inflammatory response, said composition comprising an effective analgesic or anti-inflammatory amount of a selected non-narcotic analgesic/nonsteroidal anti-inflammatory drug as defined hereinafter and an amount of caffeine sufficient to hasten the onset of the analgesic or anti-inflammatory response or to enhance the analgesic or anti-inflammatory response.

In another aspect, the present invention provides a novel pharmaceutical composition of matter for use in eliciting an analgesic response, said composition comprising an effective analgesic amount of an orally analgesically active narcotic agonist or agonist-antagonist and an amount of caffeine sufficient to hasten the onset of the analgesic response or to enhance the analgesic response.

In another aspect, the present invention proves a novel pharmaceutical composition of matter for use in eliciting an analgesic response, said composition comprising an effective analgesic amount of an orally analgesically active narcotic agonist or agonist-antagonist, an amount of a selected non-narcotic analgesic as defined hereinafter sufficient to enhance analgesia, and an amount of caffeine sufficient to further enhance analgesia or to hasten its onset.

Typically, the active ingredients of the compositions of the invention are further associated with a nontoxic pharmaceutically acceptable inert carrier therefor.

In other aspects, the invention provides methods of hastening the onset of an analgesic or anti-inflammatory response and methods of eliciting an enhanced analgesic or anti-inflammatory response in a mammal.

DETAILED DESCRIPTION OF THE INVENTION

The non-narcotic analgesics/nonsteroidal anti-inflammatory drugs for use in the compositions and methods of the present invention can be selected from the following categories:
(1) the propionic acid derivatives;
(2) the acetic acid derivatives;
(3) the fenamic acid derivatives;
(4) the biphenylcarboxylic acid derivatives; and
(5) the oxicams.
While some of these compounds are primarily used at the present time as anti-inflammatory agents and others are primarily used as analgesics, in fact all of the contemplated compounds have both analgesic and anti-inflammatory activity and can be used at appropriate dosage levels for either purpose in the compositions and methods of the present invention. The compounds in groups (1) through (4) typically contain a carboxylic acid function; however, those acids are sometimes administered in the form of their pharmaceutically acceptable salts, e.g. sodium salts.

The propionic acid derivatives for use herein include, but are not limited to, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be encompassed by this group. Presently preferred members of the propionic acid group include ibuprofen, naproxen, flurbiprofen, fenoprofen, ketoprofen and fenbufen. Structural formulas for representative group members are set forth below:

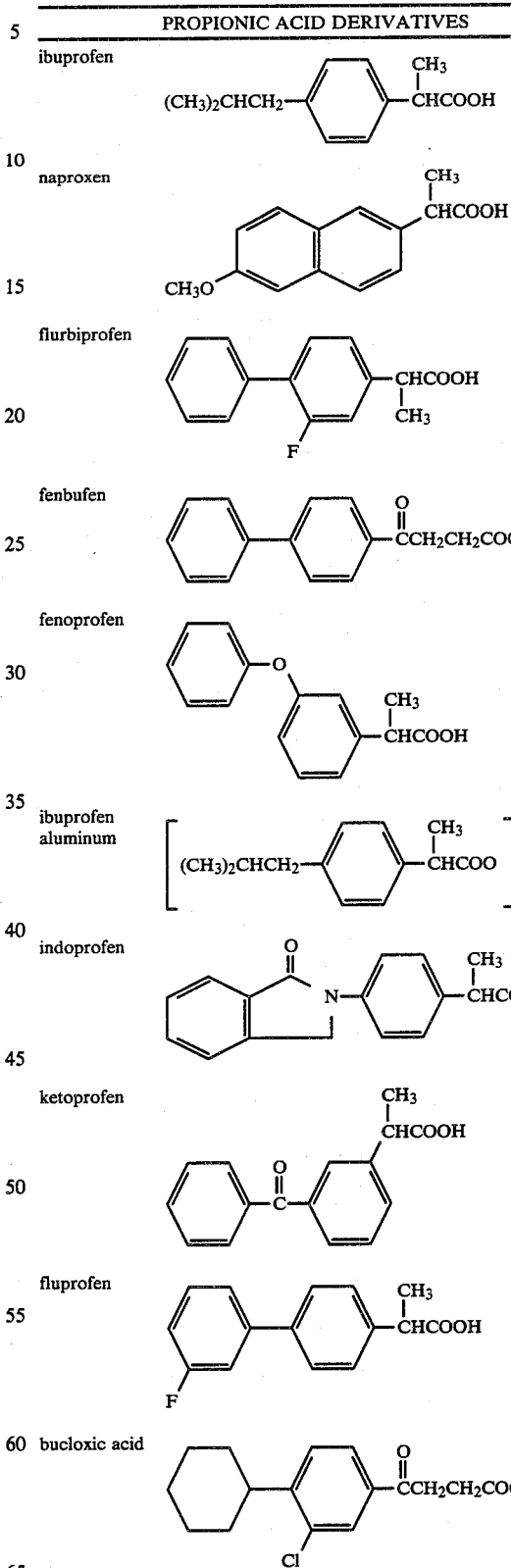

Thus, "propionic acid derivatives" as defined herein are non-narcotic analgesics/nonsteroidal anti-inflammatory drugs having a free —CH(CH₃)COOH or —CH₂CH₂COOH group (which optionally can be in the form of a pharmaceutically acceptable salt group, e.g. —CH(CH₃)COO⁻Na⁺ or —CH₂CH₂COO⁻Na⁺), typically attached directly or via a carbonyl function to a ring system, preferably to an aromatic ring system.

The acetic acid derivatives for use herein include, but are not limited to, indomethacin, sulindac, tolmetin, zomepirac, diclofenac, fenclofenac, alclofenac ibufenac, isoxepac, furofenac, tiopinac, zidometacin, acemetacin, fentiazac, clidanac and oxpinac. Structurally related acetic acid derivatives having similar analgesic and anti-inflammatory properties are also intended to be encompassed by this group. Presently preferred members of the acetic acid group include tolmetin sodium, zomepirac sodium, sulindac and indomethacin. Structural formulas for representative group members are set forth below:

ACETIC ACID DERIVATIVES

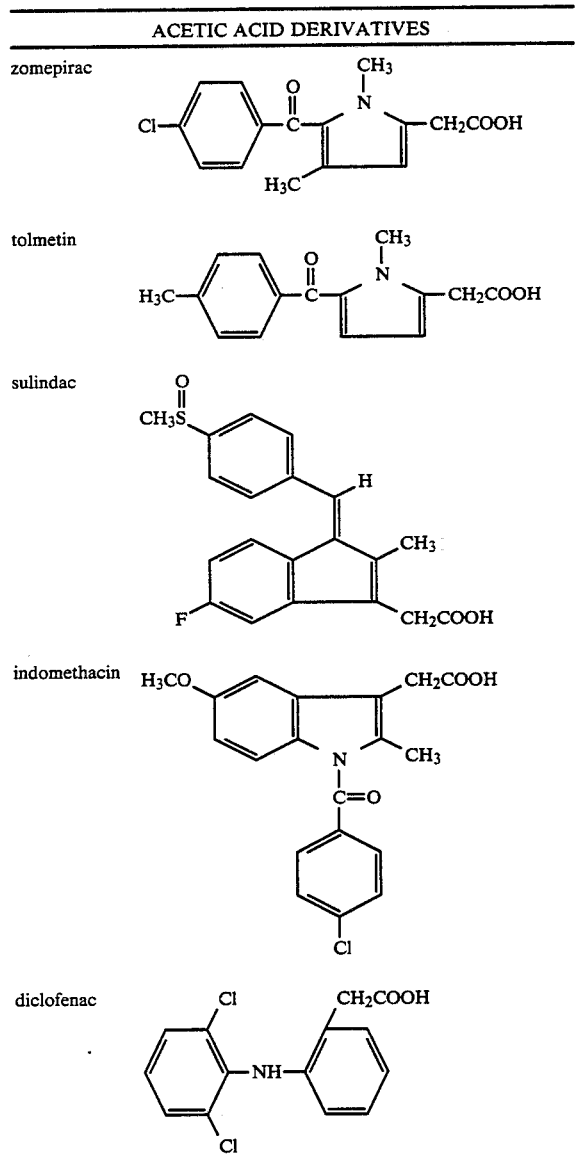

ACETIC ACID DERIVATIVES — continued alclofenac
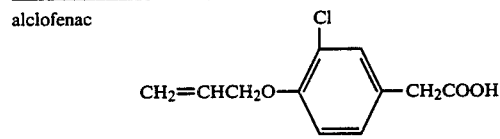

fenclozic acid
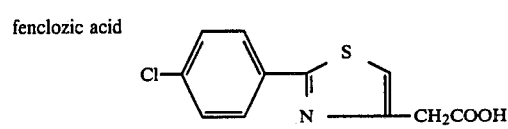

ibufenac
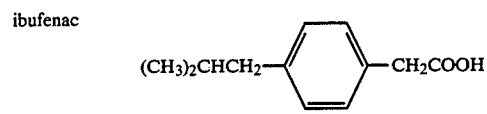

Thus, "acetic acid derivatives" as defined herein are non-narcotic analgesics/nonsteroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives for use herein include, but are not limited to, mefenamic acid, meclofenamic acid, flufenamic acid, niflumic acid and tolfenamic acid. Structurally related fenamic acid derivatives having similar analgesic and anti-inflammatory properties are also intended to be encompassed by this group. Presently preferred members of the fenamic acid group include mefenamic acid and meclofenamate sodium (meclofenamic acid, sodium salt). Structural formulas for representative group members are set forth below:

FENAMIC ACID DERIVATIVES

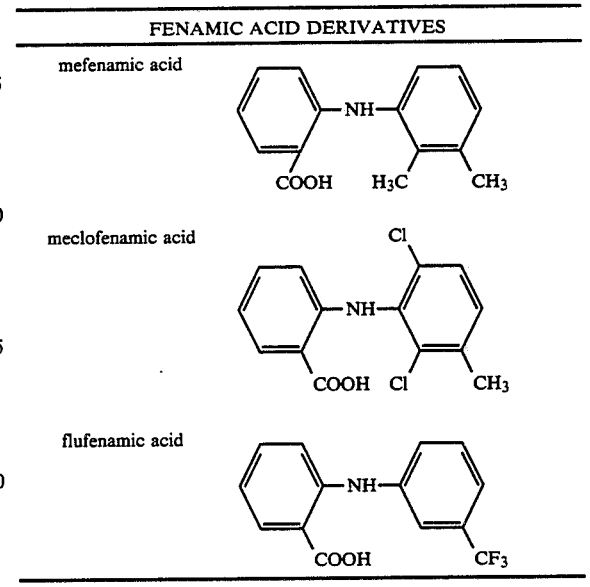

Thus, "fenamic acid derivatives" as defined herein are non-narcotic analgesics/nonsteroidal anti-inflammatory drugs which contain the basic structure

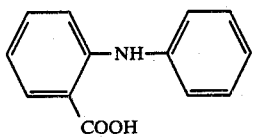

which can bear a variety of substituents and in which the free —COOH group can be in the form of a pharmaceutically acceptable salt group, e.g. —COO⁻Na⁺.

The biphenylcarboxylic acid derivatives for use herein includes, but are not limited to, diflunisal and flufenisal. Structurally related biphenylcarboxylic acid derivatives having similar analgesic and anti-inflammatory properties are also intended to be encompassed by this group. Preferred members of this group are diflunisal and flufenisal, whose structural formulas are set forth below:

| BIPHENYLCARBOXYLIC ACID DERIVATIVES | |
| --- | --- |
| diflunisal | 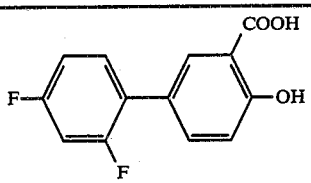 |
| flufenisal | 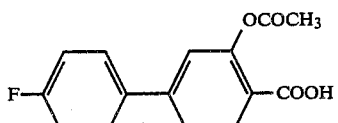 |

Thus, "biphenylcarboxylic acid derivatives" as defined herein are non-narcotic analgesics/nonsteroidal anti-inflammatory drugs which contain the basic structure

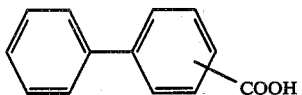

which can bear a variety of substituents and in which the free —COOH group can be in the form of a pharmaceutically acceptable salt group, e.g. —COO⁻Na⁺.

The oxicams for use herein include, but are not limited to, piroxicam, sudoxicam, isoxicam and CP-14,304. Structurally related oxicams having similar analgesic and anti-inflammatory properties are also intended to be encompassed by this group. A preferred member of this group is piroxicam; representative members are depicted below:

| OXICAMS | |
| --- | --- |
| piroxicam | 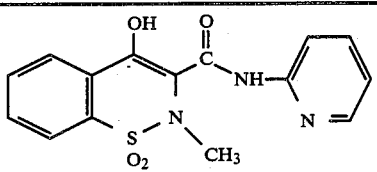 |
| sudoxicam | 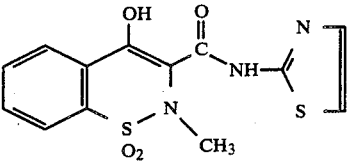 |
| isoxicam | 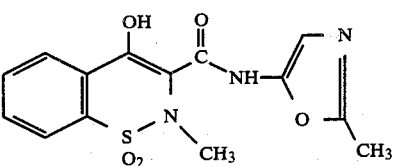 |
| CP-14,304 (4-hydroxy-1,2-benzothiazine 1,1-dioxide 4-(N—phenyl)-carboxamide] | 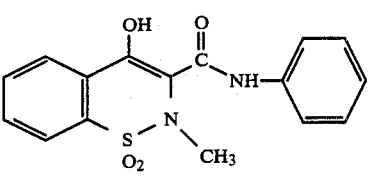 |

Thus, "oxicams" as defined herein are non-narcotic analgesics/nonsteroidal anti-inflammatory drugs which have the general formula

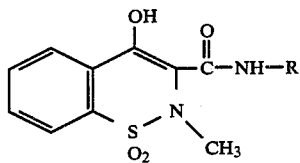

wherein R is an aryl or heteroaryl ring system.

The narcotic analgesics for use in the present invention are orally active narcotic agonists and narcotic agonist-antagonists (i.e. antagonists with analgesic properties). Suitable narcotic agonists for use herein include orally analgesically active members of the morphine group, the meperidine group and the methadone group, notably codeine, oxycodone, hydromorphone, levorphanol, meperidine, propoxyphene and methadone. Suitable agonist-antagonists for use herein include orally analgesically active antagonists of the morphine type, notably propiram and buprenorphine; and orally analgesically active antagonists of the nalorphine type, notably pentazocine, nalbuphine and butorphanol. Another suitable agonist-antagonist is meptazinol. In many instances, the narcotic analgesics for use herein are administered in the form of their pharmaceutically acceptable acid addition salts, e.g. codeine sulfate, codeine phosphate, oxycodone hydrochloride, oxycodone terephthalate, hydromorphone hydrochloride, levorphanol tartrate, meperidine hydrochloride, propoxyphene hydrochloride, propoxyphene napsylate, methadone hydrochloride, propiram fumarate, buprenorphine hydrochloride, nalbuphine hydrochloride and meptazinol hydrochloride. Structural formulas for representative free bases are shown below:

codeine 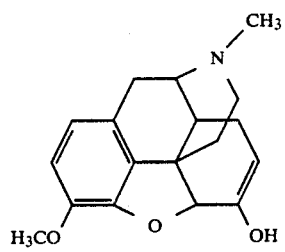
oxycodone 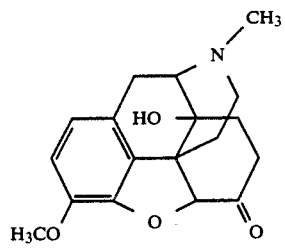
levorphanol 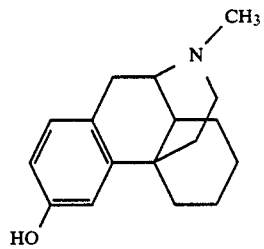
meperidine 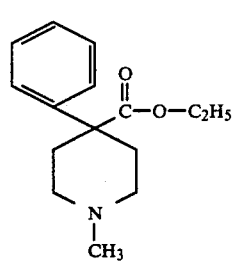
methadone 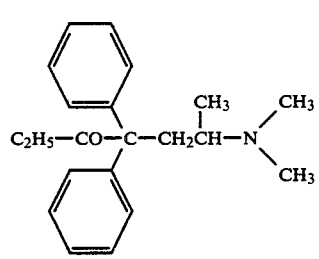
meptazinol 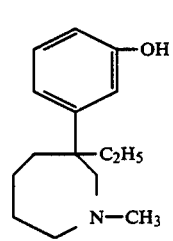
-continued
propoxyphene 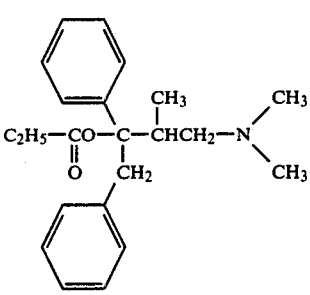
propiram 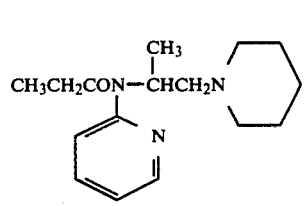
buprenorphine 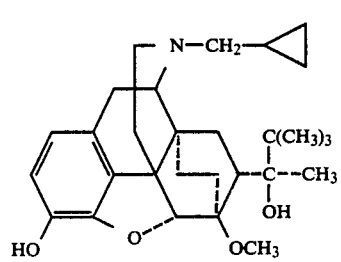
pentazocine 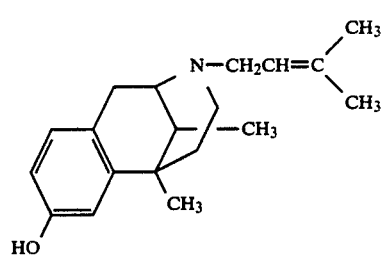
nalbuphine 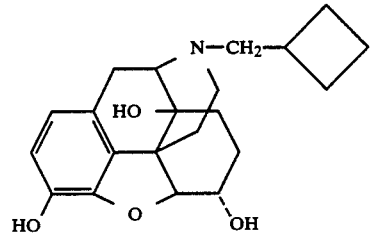
butorphanol 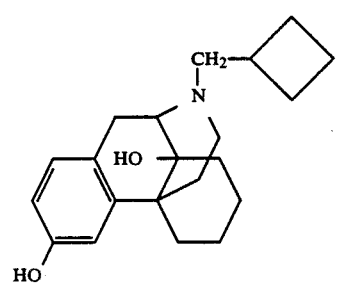

hydromorphone

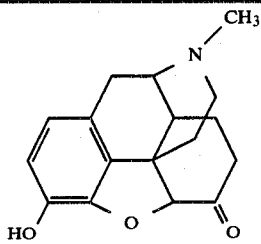

The term "caffeine" as used herein is intended to encompass not only caffeine as the anhydrous powder, but any salt or derivative of caffeine or any compounded mixture thereof which is non-toxic, pharmaceutically acceptable and which is capable of hastening and enhancing an analgesic or anti-inflammatory response when employed as described herein. See, for example, *The Merck Index*, ninth edition, Merck & Co., Inc. Rahway, N.J. (1976), pp. 207–208, for a description of caffeine salts, derivatives and mixtures which may prove useful in the compositions of the present invention. Nevertheless, caffeine as the anhydrous powder base is presently preferred and, where specific amounts of caffeine are set forth below, such amounts are given in mg of the anhydrous base.

The term "selected NSAID" as used herein is intended to mean any non-narcotic analgesic/nonsteroidal anti-inflammatory compound falling within one of the five structural categories indicated hereinabove. Similarly, the term "selected narcotic analgesic" as used herein is intended to mean any orally analgesically active narcotic analgesic, be it an orally active narcotic agonist or a narcotic antagonist having oral analgesic activity. The terms "selected NSAID" and "selected narcotic analgesic" are used for the sake of simplicity in the discussion which follows.

When a selected NSAID is combined with caffeine in accord with the present invention, the following unexpected results are produced:

(1) the analgesic or anti-inflammatory effect of the selected NSAID on the mammal is brought on more quickly;

(2) lower amounts of the selected NSAID are required for the same analgesic or anti-inflammatory effect; and (3) across all doses, a greater analgesic or anti-inflammatory response is achieved.

For patients suffering pain, the time from administration of medication to the onset of effective relief is clearly of paramount importance. The present inventors' discovery that caffeine substantially shortens the onset time (i.e. substantially hastens the onset) of analgesia is therefore very significant; moreover, it is completely unexpected. Likewise, in patients suffering inflammation, e.g. from rheumatoid arthritis or osteoarthritis, the substantial shortening of onset time provided by this invention is extremely important, not only because it provides faster relief from pain but also because it provides more rapid relief from other aspects of the inflammatory disease, e.g. morning stiffness.

Further, the ability of caffeine to enhance analgesia or to enhance the anti-inflammatory response, i.e. to substantially reduce the amount of the selected NSAID which is required to elicit a given analgesic or anti-inflammatory response, is also an unexpected and very important aspect of this invention. This unexpected and important finding permits the use of the selected NSAID in quantities substantially less than the dosages presently suggested as an analgesic or anti-inflammatory agent in humans. Use of lower doses should in turn lower the incidence and/or severity of undesirable side effects. Moreover, at a given dosage level, a greater analgesic or anti-inflammatory response can be achieved.

More specifically, it is believed that onset time for analgesia or for the anti-inflammatory response can be reached, on the average, about one-fourth to about one-third sooner when a composition of the invention is used rather than when the selected NSAID alone is employed. Also, approximately one-fifth to one-third less of the selected NSAID can be used in the caffeine combination to achieve the same analgesic or anti-inflammatory effect as that obtained by use of the selected NSAID alone; in other words, the addition of caffeine decreases the amount of the selected NSAID to about two-thirds to four-fifths of the usual amount to achieve the same effect. These ratios may vary, however, depending on the patient's individual response, the selected dosage level of the active ingredients etc.

The precise amount of non-narcotic analgesic/non-steroidal anti-inflammatory drug for use in the present compositions will vary depending, for example, on the specific drug chosen, the condition for which the drug is administered and the size and kind of the mammal. Generally speaking, the selected NSAID can be employed in any amount known to be an effective analgesic or anti-inflammatory amount, as well as at doses one-fifth to one-third lower than the usual amounts.

For humans, typical effective analgesic amounts of presently preferred NSAIDs for use in unit dose compositions of the invention are about 125 to 500 mg diflunisal, about 25 to 100 mg zomepirac sodium, about 50 to 400 mg ibuprofen, about 125 to 500 mg naproxen, about 25 to 50 mg flurbiprofen, about 50 to 200 mg fenoprofen, about 10 to 20 mg piroxicam, about 125 to 250 mg mefenamic acid, about 100 to 400 mg fenbufen or about 25 to 50 mg ketoprofen; however, greater amounts can be employed if desired. The amount of caffeine in the analgesic composition will be an amount sufficient to shorten the onset time and/or to enhance analgesia. For humans, a unit dosage analgesic composition will typically contain from about 60 to about 200 mg (preferably about 65 to about 150 mg) caffeine; this dosage level of caffeine is generally sufficient to both shorten the onset time and enhance analgesia. However, certain NSAIDs are particularly long-acting and need be administered less frequently than the usual every 4 to 6 hours; for example, diflunisal and naproxen are typically administered only twice daily and piroxicam only once a day. When such long-acting drugs are employed, it is often desirable to include an additional and analgesia-enhancing amount of caffeine in the composition in sustained release form; thus, the composition will typically contain from about 60 to about 200 (preferably about 65 to about 150) mg caffeine for immediate release to hasten onset and enhance analgesia, and one (or possibly more) additional 60 to 200 (preferably 65 to 150) mg dose(s) of caffeine for sustained release to continue enhancement of analgesia. The daily analgesic dose in humans will vary with the selected NSAID, and may of course be as low as the amount contained in a single unit dose as set forth above. The daily dose for use in the treatment of mild to moderate pain will preferably not exceed 1500 mg diflunisal or 600 mg zomepirac sodium or 2400 mg ibuprofen or 1000 mg naproxen or 150 mg flurbiprofen or 2400 mg fenoprofen or 20 mg piroxicam or 1000 mg mefenamic acid or 2400 mg fenbufen or 300 mg ketoprofen, plus 1000 mg caffeine, for use in the treatment of mild to moderate pain, although greater amounts could be employed if tolerated by the patient.

For humans, typical effective anti-inflammatory amounts of presently preferred NSAIDs for use in unit dose compositions of the invention are about 10 to 20 mg piroxicam, about 250 to 500 mg diflunisal, about 25 to 50 mg indomethacin, about 150 to 200 mg sulindac, about 200 to 400 mg tolmetin sodium, about 50 mg meclofenamate sodium, about 65 to 600 mg ibuprofen, about 250 to 500 mg naproxen, about 800 to 1200 mg fenbufen, about 50 to 100 mg ketoprofen, or about 200 to 600 mg fenoprofen; however, greater amounts can be employed if desired. The amount of caffeine in the anti-inflammatory composition will be an amount sufficient to shorten the onset time and/or to enhance the anti-inflammatory response. For humans, a unit dosage anti-inflammatory composition will typically contain from about 60 to 200 mg (preferably 65 to 150 mg) caffeine; this dosage level is generally sufficient to both shorten the onset time and enhance the anti-inflammatory response. Again, the long-acting NSAIDs, i.e. those administered less often than 3 or 4 times a day in the treatment of inflammation (e.g. piroxicam, diflunisal, sulindac, tolmetin sodium and naproxen) can be formulated with larger amounts of caffeine in the dosage unit, a portion of the caffeine being in sustained release form. Such compositions will typically contain from about 60 to 200 (preferably about 65 to 150) mg caffeine for immediate release to hasten onset and enhance the anti-inflammatory response and one or more additional 60 to 200 (preferably 65 to 150) mg doses of caffeine for sustained release to continue enhancement of the anti-inflammatory response. The daily anti-inflammatory dose in humans will vary with the selected NSAID; for example, the daily dose for use in the treatment of inflammatory conditions, e.g. rheumatoid arthritis, osteoarthritis and degenerative joint disease, will generally be about 10 to 20 mg piroxicam, about 250 to 1500 mg diflunisal, about 75 to 200 mg indomethacin, about 200 to 600 mg sulindac, about 600 to 2000 mg tolmetin sodium, about 200 to 400 mg meclofenamate sodium, about 1600 to 3000 mg ibuprofen, about 250 to 1000 mg naproxen, about 3200 to 4800 mg fenbufen, about 150 to 400 mg ketoprofen, or about 1600 to 2400 mg fenoprofen, plus 1000 mg caffeine, although greater amounts could be employed if tolerated by the patient.

When a selected narcotic analgesic is combined with caffeine in accord with the present invention, the following unexpected results are produced:

(1) the analgesic effect of the selected narcotic analgesic is brought on more quickly;
(2) lower amounts of the selected narcotic analgesic are required for the same analgesic effect; and
(3) across all doses, a greater analgesic response is achieved.

For patients suffering pain, and most especially for patients suffering severe pain, the time from administration of medication to the onset of effective relief is clearly of paramount importance. The present inventors' discovery that caffeine substantially shortens the onset time, (i.e. substantially hastens the onset) of analgesia when it is combined with a selected narcotic analgesic is therefore highly significant; moreover, it is totally unexpected.

Further, the ability of caffeine to enhance analgesia, i.e. to substantially reduce the amount of selected narcotic analgesic which is required to elicit a given analgesic response, is also an unexpected and very important aspect of this invention. This unexpected and important finding permits the use of the selected narcotic analgesic in quantities substantially less than the dosages presently suggested as an analgesic agent in humans. Use of lower doses should in turn lower the incidence and/or severity of undesirable side effects, including lessening addiction potential. Moreover, at a given dosage level, a greater analgesic response can be achieved.

More specifically, it is believed that onset time for analgesia can be reached, on the average, about one-fourth to about one-third sooner when a selected narcotic analgesic/caffeine composition of the invention is used rather than when the narcotic analgesic alone is employed. Also, approximately one-fifth to one-third less of the selected narcotic analgesic can be used in the caffeine combination to achieve the same analgesic effect as that obtained by use of the narcotic analgesic alone; in other words, the addition of caffeine decreases the amount of the selected narcotic analgesic to two-thirds to four-fifths of the usual amount to achieve the same effect. These ratios may vary, however, depending on the patient's individual response, the selected dosage level of the active ingredients etc.

The selected narcotic analgesic/caffeine compositions of the present invention are also advantageous in that the use of caffeine counteracts the sedative effects of the selected narcotic analgesic such that the patient is more alert, has better motor skills and may have an improved sense of well-being as compared to when the narcotic analgesic is administered alone.

The precise amount of selected narcotic analgesic for use in the present narcotic analgesic/caffeine compositions will vary depending, for example, on the specific drug chosen, the size and kind of the mammal and the condition for which the drug is administered. Generally speaking, the selected narcotic analgesic can be employed in any amount known to be an orally effective analgesic amount as well as at doses about one-fifth to one-third lower than the usual amounts.

For humans, typical effective analgesic amounts of presently preferred narcotics for use in unit dose narcotic analgesic/caffeine compositions of the present invention, to be administered every 4 to 6 hours as needed, are about 1 to 5 mg hydromorphone hydrochloride, about 15 to 60 mg codeine sulfate or phosphate, about 2.5 to 5 mg oxycodone hydrochloride or a mixture of oxycodone hydrochloride and oxycodone terephthalate (e.g. 4.50 mg oxycodone hydrochloride+0.38 mg oxycodone terephthalate, or 2.25 mg oxycodone hydrochloride+0.19 mg oxycodone terephthalate), about 1 to 3 mg levorphanol tartrate, about 50 mg meperidine hydrochloride, about 65 mg propoxyphene hydrochloride, about 100 mg propoxyphene napsylate, about 5 to 10 mg methadone hydrochloride, about 25 to 60 mg propiram fumarate, about 8 to 10 mg buprenorphine hydrochloride, about 25 to 50 mg pentazocine hydrochloride, about 10 to 30 mg nalbuphine hydrochloride, about 4 to 8 mg butorphanol tartrate or about 100 to 500 mg meptazinol hydrochloride. The amount of caffeine in the analgesic composition will be an amount sufficient to shorten the onset time and/or to enhance analgesia. For humans, a unit dosage analgesic composition will typically contain from about 60 to about 200 mg (preferably about 65 to 150 mg) caffeine; this dosage level of caffeine is generally sufficient to both shorten the onset time and enhance analgesia. The daily analgesic dose in humans will vary with the selected narcotic analgesic, and may of course be as low as the amount contained in a single unit dose as set forth above. The daily dose for use in the treatment of moderate to severe pain will preferably not exceed 30 mg hydromorphone hydrochloride, or 360 mg codeine sulfate or phosphate, or 60 mg oxycodone hydrochloride or hydrochloride/terephthalate mixture, or 18 mg levorphanol tartrate, or 600 mg meperidine hydrochloride, or 390 mg propoxyphene hydrochloride, or 600 mg propoxyphene napsylate, or 60 mg methadone hydrochloride, or 300 mg propiram fumarate, or 60 mg buprenorphine hydrochloride, or 300 mg pentazocine hydrochloride, or 180 mg nalbuphine hydrochloride, or 48 mg butorphanol tartrate, or 3000 mg meptazinol hydrochloride, and 1000 mg caffeine, although greater amounts could be employed if tolerated by the patient.

When a selected NSAID and a selected narcotic analgesic as defined herein are combined, enhanced analgesia results; at a given dosage level, the analgesic effect of the combination is greater than for either the selected NSAID or the selected narcotic analgesic alone. Consequently, it is possible to lower the amount of one of the analgesics and achieve the same level of analgesia as with a higher dose of that analgesic alone. Generally, it is considered more desirable to lower the dosage of the selected narcotic analgesic, since its side effects are considered more undesirable than those of the selected NSAID. The lowering of dosage of the selected narcotic analgesic leads to lower incidence and less severity of its attendant side effects, and less likelihood of addiction potential. Generally speaking, the addition of a selected NSAID can be expected to decrease the amount of the selected narcotic analgesic needed to two-thirds to four-fifths of the usual amount to achieve the same effect. These ratios may vary, however, depending on the particular drugs selected, the patient's individual response, and the selected dosage levels of the active ingredients. Moreover, it is possible to maintain the usual amount of the selected narcotic analgesic and take advantage of the enhanced analgesic response. When a selected narcotic analgesic and a selected NSAID are further combined with caffeine in accord with the present invention, the combination has all of the unexpected results (hastened onset, etc.) and has all of the advantages discussed in detail above for the selected narcotic analgesic/caffeine combination. Moreover, the selected narcotic analgesic/selected NSAID/caffeine combination shares the enhancement of analgesia made possible by the combination of the two different kinds of analgesics. Since the presence of caffeine counteracts the sedative properties of the narcotic, the resultant composition is especially of interest as a daytime oral analgesic, effective against severe pain, which can be utilized in patients who must remain alert and active.

It is believed that caffeine enhances the analgesic effect not only of the selected narcotic analgesic but also of the selected NSAID in the three-component combination; and that caffeine enhances the onset of analgesia from both of these drugs. This is likely to produce a stronger analgesic response than that produced, not only by the selected narcotic analgesic alone or the selected NSAID alone, but also by the selected NSAID/caffeine, selected narcotic analgesic/caffeine and selected narcotic analgesic/selected NSAID combinations. Nevertheless, it is not generally recommended that the amounts of selected narcotic analgesic and selected NSAID in the composition with caffeine be further reduced from those utilized in the selected narcotic analgesic/selected NSAID combination; rather, the three-component composition is intended to take advantage of the further enhanced and quicker analgesia provided by the presence of caffeine. Thus, for use in treating humans, the analgesically effective amount of selected narcotic analgesic in a unit dose three-component composition will typically be as set forth hereinabove for the two-component narcotic analgesic/caffeine compositions of the invention. The amount of selected NSAID in a unit dose three-component composition will be an amount sufficient to enhance analgesia. For humans, a unit dosage three-component composition will typically contain an amount of selected NSAID which is well tolerated alone when used to treat mild to moderate pain and which is sufficient to enhance analgesia when combined with the selected narcotic analgesic; such amounts are the same as those set forth hereinabove as effective analgesic amounts in the discussion of the selected NSAID/caffeine two-component compositions. The amount of caffeine in the three-component composition will be an amount sufficient to further enhance analgesia or to hasten its onset; in humans, this amount will typically be from about 60 to about 200 mg (preferably 65 to 150 mg), an amount generally sufficient to both hasten onset and enhance analgesia. The daily analgesic dose in humans for each analgesic in the three-component composition will generally not exceed their daily analgesic doses as disclosed hereinabove in connection with the two-component mixtures, while the daily dosage of caffeine again will generally not exceed 1000 mg. Of course, greater amounts can be used if tolerated by the patient.

The presently preferred narcotics described hereinabove for use in the narcotic analgesic/caffeine compositions are likewise preferred for use in the three-component compositions. As these preferred narcotics are typically administered every 4 to 6 hours, particularly preferred NSAIDs for use in the three-component compositions will be selected from among those preferred NSAIDs described hereinabove for use in the NSAID/caffeine compositions but which are likewise effective for 4 to 6 hour periods (zomepirac sodium, ketoprofen, ibuprofen, flurbiprofen, fenoprofen, mefenamic acid and the like). If a longer acting narcotic analgesic is employed, or if the selected narcotic analgesic is formulated in sustained release form, then one of the longer acting of the NSAIDs could be combined therewith and, if desired, additional caffeine could be included in sustained release form. Alternatively, all three components might be formulated for sustained release, in which case much larger amounts of each would be incorporated in an individual unit.

While the compositions of the invention are preferably for oral use, they may also be formulated for and administered by other methods which are known for administering analgesics, e.g. as suppositories. Also, the preferred human dosage levels indicated above are for use in adults; pediatric compositions would contain proportionately less of the active ingredients.

The compositions of the present invention are very conveniently administered to mammals by any route of administration suitable for the selected NSAID and/or selected narcotic analgesic component, e.g. oral or rectal. Preferably, the combination is formulated with any suitable nontoxic pharmaceutically acceptable inert carrier material. Such carrier materials are well known to those skilled in the art of pharmaceutical formulations. For those not skilled in the art, reference is made to the text entitled, "REMINGTON'S PHARMACEUTICAL SCIENCES" (Fourteenth Edition), 1970. In a typical preparation for oral administration, e.g., tablet or capsule, the selected NSAID in an effective analgesic or anti-inflammatory amount and caffeine in an amount sufficient to enhance the analgesic or anti-inflammatory response or to hasten its onset, or the selected narcotic analgesic in an effective analgesic amount and caffeine in an amount sufficient to enhance the analgesic response or to hasten its onset, or the selected narcotic analgesic in an effective analgesic amount together with a selected NSAID in an amount sufficient to enhance the analgesic response and caffeine in an amount sufficient to further enhance the analgesic response or to hasten its onset, are combined with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alignate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citris pulp, carboxymethylcellulose and sodium lauryl sulfate. If desired, a conventional pharmaceutically acceptable dye can be incorporated into the dosage unit form, i.e., any of the standard FD&C dyes. Sweetening and flavoring agents and preservatives can also be included, particularly when a liquid dosage form is formulated, e.g. an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. Such compositions should preferably contain at least 0.1% of active components; generally, the active ingredients will be between about 2% to about 60% of the weight of the unit.

Illustrative of typical unit dosage forms are tablets or capsules containing the amounts indicated in the table below. Note that the asterisk (*) indicates that the adjacent amount is in sustained release form, e.g. "130 mg+130 mg*" means that the first 130 mg is formulated for immediate release, while the second 130 mg is in sustained release form.

TABLE

| Selected Narcotic Analgesic | Selected NSAID | Caffeine |
|---|---|---|
| | diflunisal, | |
| | 125 mg | 130 mg + 130 mg* |
| | 250 mg | 130 mg + 130 mg* |
| | 500 mg | 130 mg + 130 mg* |
| | mg sodium, | |
| | 25 mg | or 130 mg |
| | 50 mg | 65 or 130 mg |
| | 100 mg | 65 or 130 mg |
| | ibuprofen, | |
| | 50 mg | 65 or 130 mg |
| | 100 mg | 65 or 130 mg |
| | 200 mg | 65 or 130 mg |
| | 300 mg | 65 or 130 mg |
| | 400 mg | 65 or 130 mg |
| | 500 mg | 65 or 130 mg |
| | 600 mg | 65 or 130 mg |
| | naproxen, | |
| | 125 mg | 130 mg + 130 mg* |
| | 250 mg | 130 mg + 130 mg* |
| | 250 mg | 65 mg + 65 mg* |
| | 500 mg | 130 mg + 130 mg* |
| | flurbiprofen, | |
| | 25 mg | 130 mg |
| | 50 mg | 130 mg |
| | fenoprofen, | |
| | 50 mg | 65 or 130 mg |
| | 100 mg | 130 mg |
| | 200 mg | 65 or 130 mg |
| | 300 mg | 130 mg |
| | 600 mg | 130 mg |
| | piroxicam, | |
| | 10 mg | 130 mg + 130 mg* |
| | 20 mg | 130 mg + 130 mg* |
| | 20 mg | 130 mg |
| | 20 mg | 130 mg + 260 mg* |
| | tolmetin sodium, | |
| | 200 mg | 130 mg |
| | 400 mg | 130 mg |
| | ibuprofen aluminum, | |
| | 400 mg | 130 mg |
| | mefenamic acid, | |
| | 125 mg | 65 or 130 mg |
| | 250 mg | 65 or 130 mg |
| | indomethacin, | |
| | 25 mg | 130 mg |
| | 50 mg | 130 mg |
| | ketoprofen, | |
| | 25 mg | 65 or 130 mg |
| | 50 mg | 65 or 130 mg |
| | fenbufen, | |
| | 200 mg | 65 or 130 mg |
| | 400 mg | 65 or 130 mg |
| | 800 mg | 65 or 130 mg |
| | sulindac, | |
| | 150 mg | 130 mg + 130 mg* |
| | 200 mg | 130 mg + 130 mg* |
| | meclofenamate sodium, | |
| | 50 mg | 65 or 130 mg |
| hydromorphone hydrochloride, | | |
| 1 mg | | 130 mg |
| 2 mg | | 130 mg |
| 3 mg | | 130 mg |
| 4 mg | | 130 mg |
| 5 mg | | 130 mg |
| codeine sulfate or phosphate, | | |
| 15 mg | | 130 mg |
| 30 mg | | 130 mg |
| 45 mg | | 130 mg |
| 60 mg | | 130 mg |
| oxycodone hydrochloride, | | |
| 2.5 mg | | 130 mg |
| 5 mg | | 130 mg |
| meptazinol hydrochloride, | | |
| 200 mg | | 65 or 130 mg |
| oxycodone hydrochloride/ | | |

TABLE-continued

| Selected Narcotic Analgesic | Selected NSAID | Caffeine |
|---|---|---|
| terephthalate mixture, | | |
| 4.5 mg/0.38 mg | | 130 mg |
| 2.25 mg/0.19 mg | | 130 mg |
| levorphanol tartrate, | | |
| 1 mg | | 130 mg |
| 2 mg | | 130 mg |
| 3 mg | | 130 mg |
| meperidine hydrochloride, | | |
| 50 mg | | 130 mg |
| propoxyphene hydrochloride, | | |
| 65 mg | | 130 mg |
| propoxyphene napsylate, | | |
| 100 mg | | 130 mg |
| methadone hydrochloride, | | |
| 5 mg | | 130 mg |
| 10 mg | | 130 mg |
| propiram fumarate | | |
| 35 mg | | 65 or 130 mg |
| 50 mg | | 130 mg |
| buprenorphine hydrochloride, | | |
| 8 mg | | 130 mg |
| 10 mg | | 130 mg |
| pentazocine hydrochloride, | | |
| 25 mg | | 65 or 130 mg |
| 50 mg | | 130 mg |
| nalbuphine hydrochloride, | | |
| 10 mg | | 130 mg |
| 15 mg | | 65 or 130 mg |
| 30 mg | | 130 mg |
| butorphanol tartrate, | | |
| 4 mg | | 130 mg |
| 8 mg | | 65 or 130 mg |
| nalbuphine hydrochloride, | ibuprofen, | |
| 15 mg | 200 or 400 mg | 130 mg |
| propiram fumarate, | ibuprofen, | |
| 35 mg | 200 or 400 mg | 130 mg |
| 50 mg | 200 or 400 mg | 130 mg |
| 35 mg | 200 or 400 mg | 65 mg |
| 50 mg | 200 or 400 mg | 65 mg |
| pentazocine hydrochloride, | ibuprofen, | |
| 25 mg | 200 or 400 mg | 130 mg |
| butorphanol tartrate, | ibuprofen, | |
| 8 mg | 400 mg | 130 mg |
| propiram fumarate, | zomepirac sodium, | |
| 50 mg | 50 or 100 mg | 130 mg |
| 35 mg | 50 or 100 mg | 130 mg |
| propoxyphene hydrochloride, | fenoprofen, | |
| 65 mg | 200 mg | 130 mg |
| propoxyphene napsylate, | fenoprofen, | |
| 100 mg | 200 mg | 130 mg |
| propiram fumarate, | fenbufen, | |
| 35 or 50 mg | 400 mg | 130 mg |
| 35 or 50 mg | 800 mg | 130 mg |
| 35 or 50 mg | 400 mg | 65 mg |
| propiram fumarate, | mefenamic acid, | |
| 35 mg | 250 mg | 130 mg |
| codeine sulfate or phosphate, | mefenamic acid, | |
| 30 mg | 250 mg | 130 mg |
| 30 mg | 125 mg | 130 mg |
| propiram fumarate, | ketoprofen, | |
| 35 mg | 25 or 50 mg | 130 mg |
| meptazinol hydrochloride, | ketoprofen, | |
| 200 mg | 25 or 50 mg | 130 mg |
| 200 mg | 25 or 50 mg | 65 mg |

If desired, compositions of the present invention may be formulated for parenteral use by known methods. The two-component selected narcotic analgesic/caffeine composition is of particular value in the case of patients suffering severe pain who cannot tolerate such medication administered orally.

It is also possible to formulate the oral compositions of the invention in such a manner that the possibility that the narcotic analgesic could be extracted therefrom and then abused parenterally will be significantly reduced. This may be accomplished by combining the drugs with insoluble excipients such as methylcellulose to form a dosage form that is insoluble in water. Such water-insoluble oral dosage forms are already known for at least some of the narcotics themselves, e.g. for propiram fumarate and methadone hydrochloride.

The analgesic and anti-inflammatory effects of the compositions of the present invention can be quantitatively evaluated in animals in the tests described below:

Antiphenylquinone Writhing Test

This test is a standard procedure for detecting and comparing analgesic activity and generally correlates well with human efficacy.

Mice are first dosed with the medications studied. The medications used are two dose levels of a selected NSAID with and without caffeine, or of a selected narcotic analgesic with and without caffeine, or of a selected narcotic analgesic+a selected NSAID with and without caffeine. The mice are then challenged with phenyl-p-benzoquinone given intraperitoneally and observed for the characteristic stretch-writhing syndrome. Lack of writhing constitutes a positive response. The degree of analgesic protection can be calculated on the basis of suppression of writhing relative to control animals run the same day. Time response data are also obtained. The test is a modification from the methods of Sigmund et al and Blumberg et al (Sigmund, E., Cadmus, R., and Lu, G., *Proc. Soc. Exp. Biol. and Med.* 95, 729–731, 1957; Blumberg, H. et al, *Proc Soc. Exp. Biol. Med.* 118, 763–766, 1965).

The Inflamed Rat Paw Test

Pressure Induced Stimuli

The method of Randall-Selitto, modified according to Winter et al is used to ascertain the escape response threshold resulting from the application of increasing pressure to the yeast inflamed left hind paw. Drug treatment is given. The medications studied are two dose levels of a selected NSAID with and without caffeine. A constantly increasing force is applied to the paw and the "flight reaction" is observed and recorded (Randall, L. Q., and Selitto, J. J.: *Arch. Int. Pharmacodyn., II,* 409–419, 1957; Winter, C. A., and Lars, F.: *J. Pharmacol. Exp. Therap.,* 148, 373–379, 1965).

The Mouse Tail-flick Test

Tail-flick testing in mice is modified after D'Amour and Smith, using controlled high intensity heat applied to the tail. Normal and drug-treated mice are observed and the reaction time is measured. The drugs used are two doses of a selected narcotic analgesic with and without caffeine. (D'Amour, E., and Smith, L., *J. Pharmacol.,* 72, 74–79, 1941).

Haffner Tail-Pinch Method

A modification of the procedure of Haffner is used to ascertain drug effects on the aggressive attacking responses elicited by a pressure stimulus pinching the tail of a rat. A clamp is on the base of each rat's tail prior to drug treatment and again at specified intervals after treatment. The time required to elicit clear attacking and biting behavior directed towards the stimulus is observed. The medications stuided are two doses of a selected narcotic analgesic with and without caffeine. (Haffner, F.: *Experimentelle Prufung Schmerzstillender Mittel. Deutsch med. Wschr.*, 55, 731–732, 1929).

Mouse Hot-Plate Test (Thermal Stimuli)

A modification of the method of Woolfe and Mac-Donald is used and involves the application of a controlled heat stimulus to the paws of mice. Drug is administered to the treatment group. The latency between the time of the animal's contact with the hot-plate and the observation of the standard pain response, jumping and/or rapid patting of one or both hind paws is measured. The medications studied are two doses of a selected narcotic analgesic with and without caffeine. (Woolfe, G., and MacDonald, A. D.: *J. Pharmacol. Exp. Ther.*, 80, 300–307, 1944).

Adjuvant Arthritis Test

Adjuvant arthritis in the rat is a widely used model for human rheumatoid arthritis. It is basically an immunological reaction, involving a cellular immune response to an injected bacterial adjuvant. The response is systemic, but develops mainly in the limbs as a polyarthritis. The degree of arthritis in the hind legs is assessed either visually or by measuring the foot volume of the 21st day after injection of the adjuvant.

A single subcutaneous injection of 1 mg *Mycobacterium butyricum* suspended in 0.1 ml mineral oil is injected into the right hindpaws of rats. The swelling of the injected hind leg measured on day 16 constitutes the secondary response. Drugs are administered p.o. daily, beginning 1 day prior to injection of adjuvant. The medications used are two dose levels of selected NSAID with and without caffeine. Results are expressed as percent suppression of the control. [Walz, D. T., Di Martino, M. J., and Misher, A.: *Ann. Rheum. Dis.*, 30, 303–306 (1971)].

To establish the efficacy of the compositions of this invention in humans, patients with moderate to severe pain requiring an oral analgesic can be administered a selected narcotic analgesic or NSAID with and without caffeine or a selected narcotic analgesic+a selected NSAID with and without caffeine, while patients suffering from inflammatory or degenerative joint disease, e.g., rheumatoid arthritis, osteoarthritis, gout or acute musculo-skeletal disease requiring an oral anti-inflammatory agent, can be administered a selected NSAID with and without caffeine. To determine analgesic efficacy, a nurse observer interviews the patients as to their level of pain or stiffness and swelling at subsequent periods of time. Patients are asked to subjectively estimate the time at which the medication begins to provide relief. Appropriate statistical methods can be used to show that on the average the compositions with caffeine have shorter onset and are more efficacious. (Laska, E., Gormely, M., Sunshine, A., Belleville, J. W., Kantor, T., Forrest, W. H., Siegel, C., and Meisner, M.: "A Bioassay Computer Program for Analgesic Clinical Trials", *Clin. Pharmacol. Ther.* 8: 658, 1967; Cox, D. R., "Regression Models and Life Tables", *Journal Royal Statistical Society*, Series B, Volume 34: 187–202, 1972). Evaluation of efficacy in inflammatory and degenerative joint disease is accomplished by patient's self-assessment of severity of pain, duration of morning stiffness, general feeling, and ease of movement; and by physician's evaluation of objective measures such as tenderness, swelling, number of painful joints, plus various tests of function such as grip strength, speed of walking, chest expansion and finger to floor.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be, within the full range of equivalence of the following claims.

What we claim is:

1. A method for eliciting an onset hastened and enhanced analgesic or anti-inflammatory response in a mammal, comprising administering to said mammal a pharmaceutical composition comprising:
   (a) an analgesically and anti-inflammatorily effective amount of a non-steroidal anti-inflammatory drug comprising an acetic acid derivative or a pharmaceutically acceptable salt thereof selected from tolmetin and indomethacin; and
   (b)d an amount of caffeine sufficient to hasten the onset of and enhance the analgesic or anti-inflammatory response.

2. A method according to claim 1, wherein the non-steroidal anti-inflammatory drug is tolmetin.

3. A method according to claim 1, wherein the non-steroidal anti-inflammatory drug is indomethacin.

4. A method according to claim 1, comprising from about 60 mg and about 200 mg caffeine.

5. A method according to claim 4, comprising from about 65 mg to about 150 mg caffeine.

6. A method according to claim 1, comprising from about 25 mg to about 400 mg of said acetic acid derivative or pharmaceutically salt thereof and from about 60 mg to about 200 mg caffeine.

7. A method according to claim 2, comprising from about 200 mg to about 400 mg tolmetin or pharmaceutically acceptable salt thereof and from about 60 mg to about 200 mg caffeine.

8. A method according to claim 3, comprising from about 125 mg to about 50 mg indomethacin or pharmaceutically acceptable salt thereof and from about 60 mg to about 200 mg caffeine.

9. A method according to claim 2, wherein said tolmetin or pharmaceutically acceptable salt thereof is tolmetin sodium.

10. A pharmaceutical composition of matter for use in eliciting an onset hastened or enhanced analgesic or anti-inflammatory response in a mammal, said composition comprising:
    (a) an analgesically and anti-inflammatorily effective amount of a non-steroidal anti-inflammatory drug comprising an acetic acid derivative or pharmaceutically acceptable salt thereof selected from tolmetin and indomethacin; and
    (b) an amount of caffeine sufficient to hasten the onset of and enhance the analgesic or anti-inflammatory response.

11. A pharmaceutical composition according to claim 10, wherein the non-steroidal anti-inflammatory drug is tolmetin.

12. A pharmaceutical composition according to claim 10, wherein the non-steroidal anti-inflammatory drug is indomethacin.

13. A pharmaceutical composition according to claim 10, comprising from about 60 mg to about 200 mg caffeine.

14. A pharmaceutical composition according to claim 13, comprising about 65 mg to about 150 mg caffeine.

15. A pharmaceutical composition according to claim 10, comprising from about 25 mg to about 400 mg of said acetic acid derivative or pharmaceutically acceptable salt thereof and from about 60 mg to about 200 mg. caffeine.

16. A pharmaceutical composition according to claim 11, comprising from about 200 mg to about 400 mg tolmetin or pharmaceutically acceptable salt thereof and from about 60 mg to about 200 mg caffeine.

17. A pharmaceutical composition according to claim 12, comprising from about 25 mg to about 50 mg indomethacin or pharmaceutically acceptable salt thereof and from 60 mg to about 200 mg caffeine.

18. A pharmaceutical composition according to claim 11, wherein said tolmetin or pharmaceutically acceptable salt thereof is tolmetin sodium.

19. A pharmaceutical composition according to claim 10, further comprising a pharmaceutically acceptable inert carrier.

20. A pharmaceutical composition according to claim 19, said composition being adapted for oral administration.

21. A pharmaceutical composition according to claim 20, said composition being formulated as a tablet or capsule.

22. A pharmaceutical composition according to claim 19, wherein said composition is in sustained release form.

23. A pharmaceutical composition according to claim 19, said composition being adapted for rectal administration.

24. A pharmaceutical composition according to claim 23, said composition being formulated as a suppository.

* * * * *